US010150980B2

United States Patent
Ben Chaabane et al.

(10) Patent No.: US 10,150,980 B2
(45) Date of Patent: Dec. 11, 2018

(54) USE OF $CO_2$ TO DEACTIVATING A CELLULOLYTIC MICROORGANISM USED IN THE BIOCHEMICAL CONVERSION OF LIGNOCELLULOSIC MATERIALS

(71) Applicant: IFP Energies nouvelles, Rueil-Malmaison (FR)

(72) Inventors: Fadhel Ben Chaabane, Paris (FR); Sylvain Louret, Lyons (FR)

(73) Assignees: L'Institut National de la Recherche Agronomique, Paris (FR); Agro Industrie Recherches et Developpements, Pomacle (FR)

( * ) Notice: Subject to any disclaimer, the term of this patent is extended or adjusted under 35 U.S.C. 154(b) by 633 days.

(21) Appl. No.: 14/409,207

(22) PCT Filed: Jun. 5, 2013

(86) PCT No.: PCT/FR2013/051269
§ 371 (c)(1),
(2) Date: Dec. 18, 2014

(87) PCT Pub. No.: WO2013/190203
PCT Pub. Date: Dec. 27, 2013

(65) Prior Publication Data
US 2015/0191757 A1    Jul. 9, 2015

(30) Foreign Application Priority Data
Jun. 18, 2012  (FR) ..................... 12 01732

(51) Int. Cl.
| | |
|---|---|
| *C12P 19/14* | (2006.01) |
| *C12N 1/00* | (2006.01) |
| *C12N 9/42* | (2006.01) |
| *C12N 9/96* | (2006.01) |
| *C12P 7/10* | (2006.01) |
| *C12N 1/36* | (2006.01) |
| *C12P 19/02* | (2006.01) |
| *C13K 1/02* | (2006.01) |

(52) U.S. Cl.
CPC .............. *C12P 19/14* (2013.01); *C12N 1/005* (2013.01); *C12N 1/36* (2013.01); *C12N 9/2437* (2013.01); *C12N 9/96* (2013.01); *C12P 7/10* (2013.01); *C12P 19/02* (2013.01); *C13K 1/02* (2013.01); *Y02E 50/16* (2013.01)

(58) Field of Classification Search
CPC ....... Y02E 50/16; Y02E 50/343; Y02E 50/17; Y02E 50/13; C12P 19/14; C12P 7/10; C12P 2201/00; C12P 2203/00; C12P 7/06; C12P 7/08; C12N 9/2437; A23K 10/12; A23K 10/32; C13K 1/02

See application file for complete search history.

(56) References Cited

U.S. PATENT DOCUMENTS

| | | | |
|---|---|---|---|
| 5,141,861 A * | 8/1992 | Dale .................. | C12P 7/14 203/DIG. 13 |
| 2008/0213144 A1* | 9/2008 | Howard ............... | C12P 7/06 423/210 |

OTHER PUBLICATIONS

Cardona et al. Fuel ethanol production: process design trends and integration opportunities. Bioresource Technology. 2007;98:2415-2457.*
Olofsson et al. A short review on SSF—an interesting process option for ethanol production from lignocellulosic feedstocks. Biotechnology for Biofuels. 2008;1:1-14.*
Mitchinson, C., "Improved cellulases for the biorefinery: a review of genencor's progress in the DOE subcontract for cellulase cost reduction for bioethanol", Stanford GCEP Biomass Energy Workshop, Apr. 2004.
Schell D.J. et al., "Whole Broth Cellulase Production for Use in Simultaneous Saccharification and Fermentation", Applied Biochemistry and Biotechnology, Humana Press, Inc., vol. 24-25, pp. 287-298, No. Spring-Summer, 1990.
Reese, Elwyn T. et al., "Stability of the Cellulase of Trichoderma reesei under use conditions", Biotechnology and Bioengineering, vol. 22, No. 2, pp. 323-335, 1980.
Cardona et al., "Fuel ethanol production: Process design trends and integration opportunities", Bioresource Technology, Elsevier BV, GB, vol. 98. No. 12, pp. 2415-2457, Mar. 19, 2007.
Podkaminer, Kara K. et al., "Ethanol and anaerobic conditions reversibly inhibit commercial cellulase activity in thermopohilic simultaneous saccharirfication and fermentation (tSSF)", Biotechnology for Biofuels, vol. 5, No. 1, p. 43, Jun. 15, 2012.
McIntyre, M. et al., "Dissolved carbon dioxide effects on morphology, growth, and citrate production in Aspergillus niger A60", Enzyme and Microbial Technology, vol. 20., No. 2, pp. 135-142, Feb. 1997.
McIntyre, M. et al., "Morphogenetic and biochemical effects of dissolved carbon dioxide on filamentous fungi in submerged cultivation", Applied Microbiology and Biotechnology, vol. 50, No. 3, pp. 291-298, Sep. 18, 1998.
International Search Report for PCT/FR2013/051269 dated Sep. 17, 2013.

* cited by examiner

*Primary Examiner* — Lynn Y Fan
(74) *Attorney, Agent, or Firm* — Millen White Zelano and Branigan, PC; John Sopp

(57) ABSTRACT

The invention concerns a process for deactivating a cellulolytic microorganism enabling the production of an enzymatic cocktail, said cocktail being used without separating the cellulolytic microorganism during the biochemical conversion of lignocellulosic materials, comprising at least one step for bringing a gaseous stream into contact with a medium containing said microorganism, said gaseous stream comprising more than 25% by weight of $CO_2$ and comprising less than 0.5 molar % of $O_2$.

12 Claims, No Drawings

USE OF $CO_2$ TO DEACTIVATING A CELLULOLYTIC MICROORGANISM USED IN THE BIOCHEMICAL CONVERSION OF LIGNOCELLULOSIC MATERIALS

FIELD OF THE INVENTION

The present invention relates to producing cellulolytic and hemicellulolytic enzymes, in particular in the context of producing ethanol from cellulosic or lignocellulosic materials.

PRIOR ART

Since the 1970s, the transformation of lignocellulosic materials into ethanol, after hydrolysis of the constituent polysaccharides into fermentable sugars has been the focus of a great many studies. Examples which may be cited are the reference works from the National Renewable Energy Laboratory (Process Design and Economics for Biochemical Conversion of Lignocellulosic Biomass to Ethanol, Humbird et al., NREL/TP-5100-57764, May 2011).

Lignocellulosic materials are cellulosic materials, i.e. containing more than 90% by weight of cellulose, and/or lignocellulosic materials, i.e. constituted by cellulose, hemicelluloses, which are polysaccharides essentially constituted by pentoses and hexoses and lignin, which is a macromolecule with a complex structure and a high molecular weight, composed of aromatic alcohols bonded via ether bonds.

Wood, straw and corn cobs are the most widely used lignocellulosic materials, but other sources, dedicated forest cultures, residues of alcoholigenic, sugar and cereal plants, products and residues from the papermaking industry and transformation products of lignocellulosic materials may be used. They are mostly constituted by approximately 35% to 50% of cellulose, 20% to 30% of hemicellulose and 15% to 25% of lignin.

The process for the biochemical transformation of lignocellulosic materials into ethanol comprises a step for physico-chemical pre-treatment followed by a step for enzymatic hydrolysis using an enzymatic cocktail, a step for ethanolic fermentation of the liberated sugars, and a step for purifying the ethanol.

Ethanolic fermentation and enzymatic hydrolysis, also known as saccharification, can be carried out simultaneously (Simultaneous Saccharification and Fermentation, or SSF), for example by adding ethanolic organisms during the hydrolysis step.

The enzymatic cocktail is a mixture of cellulolytic (also known as cellulases) and/or hemicellulolytic enzymes. The cellulolytic enzymes have three main types of activities: endoglucanases, exoglucanases and cellobiases, these latter also being known as β-glucosidases. Hemicellulolytic enzymes in particular have xylanase activities.

Enzymatic hydrolysis is efficient and is carried out under mild conditions. In contrast, the cost of enzymes is still high, representing 20% to 50% of the cost of transforming lignocellulosic material into ethanol. For this reason, a great many studies have been carried out concerning reducing this cost: optimization of enzyme production initially, by selecting hyperproductive microorganisms and by improving the processes for producing said enzymes, reducing the quantity of enzymes in hydrolysis then, by optimizing the pre-treatment step, by improving the specific activity of these enzymes, and by optimizing the implementation of the enzymatic hydrolysis step.

The step for producing the enzymatic cocktail comprises three major phases: a phase (a) for growth of a cellulolytic microorganism; a phase (b) for producing an enzymatic cocktail and a phase (c) for separation and concentration, during which the enzymatic cocktail is separated from the cellulolytic microorganism and concentrated. Separation of the enzymatic cocktail and the cellulolytic microorganism is carried out by liquid/solid separation (for example by centrifuging). The enzymatic cocktail is concentrated by filtration (for example by ultrafiltration).

These separation phases are necessary, because if it is left in the presence of the enzymatic cocktail and in the absence of a carbonaceous substrate, there is a risk that the cellulolytic microorganisms will consume the enzymes contained in said cocktail so that it can survive, thereby resulting in a loss of production.

In addition, irrespective of the care taken during the separation, a portion of the enzymatic cocktail will always be lost with the fraction containing the microorganism. Depending on the separation technologies which are employed, these losses may correspond to 3% to 50% by weight of the enzymatic cocktail present before separation. Thus, it could be advantageous to use the mash without separation in order to prevent such losses.

The operating temperatures for a SSF step are of the order of 30° C. to 35° C. However, these temperatures are compatible with growth of the cellulolytic microorganisms. Thus, if the use of the enzymatic cocktail is envisaged in a SSF step without separating the cellulolytic microorganism, there is a risk of competition between the cellulolytic microorganism and the yeast used for fermentation, resulting in a reduction in the yield for said SSF step. In fact, a portion of the glucose liberated by hydrolysis will be consumed by the cellulolytic microorganism.

Thus, it would be advantageous to be able to deactivate the cellulolytic microorganism so that a step for separation of the enzymatic cocktail and said cellulolytic microorganism is no longer necessary with a view to storage and/or use thereof in a SSF step. It would also be advantageous to be able to deactivate this microorganism by using a means which is internal to the process, for example a product of one of the steps of the process.

GB 1 489 145 discloses the culture of cellulolytic microorganism and enzymes from cellulose residues, as well as the use of the culture medium/enzyme production ensemble without separating any of the constituents for enzymatic hydrolysis. They assert that the use of the whole of the medium "in accordance with the invention" without treatment (filtration, concentration or other) other than possibly adjusting the pH can improve hydrolysis of the cellulose in terms of rate and yield.

That patent is silent as to the potential problem of growth of the cellulolytic microorganism *T. reesei* under the enzymatic hydrolysis conditions, nor of the re-consumption of proteins by the cellulolytic organism. In fact, the enzymatic hydrolysis is generally carried out at temperatures which prevent the growth of the cellulolytic microorganism (between 45° C. and 55° C.), in contrast to SSF, which is carried out at temperatures in the range 30° C. to 35° C.

Barta et al. ("Process Design and Economics of On-Site Cellulase Production on Various Carbon Sources in a Softwood-Based Ethanol Plant", Enzyme Research, Vol. 2010, doi:10.4061/2010/734182) discloses the addition of all of the medium containing the cellulolytic microorganism to the SSF step. According to the authors, this does not cause a problem, as the SSF is carried out at 37° C., while growth of the cellulolytic microorganism is completely inhibited when the temperature exceeds 35° C. That postulate is questionable, as some species of *Trichoderma* (*T. pseudokoningii*, *T. saturnisporum* for example) are known to be capable of developing at up to 40-41° C.

However, the Applicant's studies have led to the discovery that certain streams which are internal to the process for the biochemical conversion of biomass to ethanol can be used to deactivate the cellulolytic microorganism.

The present invention proposes a process allowing the deactivation of a cellulolytic microorganism which overcomes the disadvantages which have arisen until now.

SUMMARY AND ADVANTAGE OF THE INVENTION

In deactivating the cellulolytic microorganism by contacting with a gas stream which is internal to the process for biochemical conversion of biomass to ethanol containing less than 0.5 molar % of oxygen, the need for separating said microorganism from the enzymatic cocktail produced is dispensed with.

A judicious choice of the internal gaseous stream used means that any negative impact on the performances of the process which could be caused by the accumulation of unwanted species by a recycling effect can be avoided.

One advantage of the process of the invention is thus that the losses of the enzymatic cocktail produced are limited. Another advantage is that the size of the facilities is limited: by limiting the losses, the over-production required to compensate for said losses is limited. Another advantage is that discharges are limited by minimizing or even dispensing with cleaning phases during the enzymatic cocktail/cellulolytic microorganism separations. Another advantage is that the risks of contamination are minimized by limiting or even dispensing with enzymatic cocktail/cellulolytic microorganism separation phases.

The advantages of the present invention, which will be listed here in a manner which is not exhaustive, mean that the cost of producing ethanol from lignocellulosic materials can be reduced, improving the competitive position of this sector.

DETAILED DESCRIPTION OF THE INVENTION

The invention concerns a process for deactivating a cellulolytic microorganism enabling the production of an enzymatic cocktail, said cocktail being used without separating the cellulolytic microorganism during the biochemical conversion of lignocellulosic materials, comprising at least one step for bringing a gaseous stream into contact with a medium containing said microorganism, said gaseous stream comprising more than 25% by weight of $CO_2$ and comprising less than 0.5 molar % of $O_2$.

Preferably, said gaseous stream originates from a SSF step.

Preferably, said gaseous stream has undergone a treatment for reducing its ethanol and volatile organic compounds content by at least 25% before the contact step.

Preferably, said treatment is washing said gaseous stream with water.

Preferably, said contact step is carried out in a SSF step.

Preferably, said contact step is carried out in the enzymatic cocktail production step at the end of the phase for production of said cocktail.

Preferably, said contact step is carried out between the enzymatic cocktail production step and a SSF step.

Preferably, the cellulolytic microorganism is selected from strains of fungi belonging to the genera *Trichoderma*, *Aspergillus*, *Penicillium* or *Schizophyllum*.

Preferably, the cellulolytic microorganism belongs to the species *Trichoderma reesei*.

The enzymatic cocktail production step employs a cellulolytic microorganism. Said production process is carried out in submerged culture. The term "submerged culture" means culture in a liquid medium.

The cellulolytic microorganisms used in the process for producing an enzymatic cocktail are strains of fungi belonging to the genera *Trichoderma*, *Aspergillus*, *Penicillium* or *Schizophyllum*, preferably belonging to the species *Trichoderma reesei*. The best performing industrial strains are strains belonging to the species *Trichoderma reesei*, modified to improve the enzymatic cocktail by mutation-selection processes such as, for example, the strain IFP CL847 (French patent FR-B-2 555 803). Strains improved by genetic recombination techniques may also be used. These strains are cultivated in stirred, aerated reactors under conditions compatible with their growth and production of enzymes.

In accordance with the invention, a gaseous stream comprising less than 0.5 molar % of oxygen ($O_2$), preferably less than 0.25 molar %, and more preferably free of oxygen, is then brought into contact with the medium containing said cellulolytic microorganism.

Alcoholic fermentation is a biochemical reaction during which organisms, for example the yeast *Saccharomyces cerevisiae*, transform sugars into ethanol and carbon dioxide ($CO_2$).

A stream of gas comprising the $CO_2$ produced during the alcoholic fermentation step and/or during the SSF step is separated during fermentation by continuously degassing the fermenter. A gas stream comprising the fraction of $CO_2$ dissolved in the fermentation medium is produced during the ethanol purification step.

The gaseous stream used in the present invention is advantageously constituted by a mixture of the gaseous stream separated by continuously degassing the fermenter and a stream produced during the ethanol purification step.

The gas stream produced during the alcoholic fermentation step comprises at least 25% by weight of $CO_2$, preferably at least 50% by weight, and more preferably at least 75% by weight. Said gaseous stream also comprises in the range 0 to 10% by weight of ethanol, preferably in the range 0 to 5% by weight. Said gaseous stream also comprises water and volatile organic compounds (VOC), these latter being defined in accordance with Article 2 of Council Directive 1999/13/CE of 11 Mar. 1999.

During said ethanol purification step, said dissolved fraction of $CO_2$ is separated from the medium containing the ethanol by any means known to the skilled person, for example by flashing, which consists of reducing the pressure of the medium to vaporize the dissolved $CO_2$, by distillation, by membrane separation or by a combination of these means or other means known to the skilled person.

Preferably, the gaseous stream containing the $CO_2$ separated by continuous degassing and/or the gaseous stream containing $CO_2$ separated in the ethanol purification step is treated in a scrubbing step so as to reduce its ethanol and VOC content as well as its oxygen content, if necessary. Said scrubbing step may be carried out using any method known to the skilled person. Preferably, said scrubbing step is washing with water or membrane separation.

Said scrubbing step is intended to reduce the ethanol and VOC content in the gaseous stream by 25% to 100%, preferably by 50% to 100% and more preferably by 75% to 100%.

In a preferred arrangement, the gaseous stream is brought into contact with the medium containing the cellulolytic microorganism without prior treatment in said scrubbing step.

During said contact, the ethanol which might be contained in said gaseous stream is absorbed into said medium containing the cellulolytic microorganism. By recycling, then, the concentration of ethanol at the end of the alcoholic fermentation step is increased. This increase in the concentration of ethanol has the effect of reducing the energy consumption of the ethanol purification step.

During said contact step, the $CO_2$ will acidify the medium. Contact of the gaseous stream and the medium containing the cellulolytic microorganism is always carried out with a check and possible adjustment of the pH.

Contact of the gaseous stream and the medium containing the cellulolytic microorganism, said medium behaving in a similar manner to a liquid, may be carried out by any means for bringing a gas and a liquid into intimate contact which is known to the skilled person. Means of this type are described, for example, but not in an exhaustive manner, in "Adsorption en traitement d'air" [Adsorption in air treatment], Michel Roustan, Techniques d'ingénieur, G1750.

Preferably, the step for bringing the gaseous stream into contact with the medium containing the cellulolytic microorganism is carried out in a SSF step. In order to obtain this contact, the equipment in which a SSF step is carried out is provided with a system for dispersing gas in the liquid medium. Another method consists of extracting a fraction of the reaction medium contained in said equipment, intimately mixing said fraction with said gaseous stream and reintroducing said fraction, which may or may not have been freed from the gaseous portion, into said equipment. Another method consists of injecting said gaseous stream into the gas overhead of said equipment.

Preferably, the step for bringing the gaseous stream into contact with the medium containing the cellulolytic microorganism is carried out during the step for producing the enzymatic cocktail, at the end of phase (b) for producing said cocktail. Since the equipment for producing the enzymatic cocktail is aerated and stirred, as is known to the skilled person and described, for example, in patent EP 1 690 944, air injection is cut off at the end of said production phase (b) and instead, said gaseous stream is injected until the partial pressure of oxygen is less than 0.5 molar %, preferably less than 0.25 molar % and more preferably 0%. Another advantage of adding $CO_2$ is to allow the pH to be reduced, preferably to between 3.5 and 3.7. These low pHs mean that the risk of contamination with respect to the culture pH, which is in the range 4.8 to 4, can be limited. Care should be taken in this step that the pH does not fall below 3.3, which would have a negative effect on the activity of certain enzymes of the cocktail.

Preferably, the step for bringing the gaseous stream into contact with the medium containing the cellulolytic microorganism is carried out between the step for producing the enzymatic cocktail and the SSF step. This contact may be brought about in dedicated equipment using conventional gas/liquid contact technologies which are known to the skilled person.

The gaseous stream containing the $CO_2$ may also be used for the production of microalgae intended for the production of a biofuel known as "third generation" fuel after extracting the lipids from said microalgae, thus meaning that a co-product with a high added value can be produced, i.e. directly for carrying out aquaculture.

Other gaseous streams comprising less than 0.5 molar % oxygen may also be used, for example effluents from units for the anaerobic treatment of water, waste combustion fumes, or effluents from organic waste methanation units.

The following examples illustrate the invention without limiting its scope. Hereinbelow, the activity of the enzymatic cocktail was measured in Filter Paper Units denoted FPU. This activity was measured on Whatman No 1 paper (procedure recommended by the IUPAC biotechnology commission) at an initial concentration of 50 g/L; a sample of the enzymatic solution to be analysed which released the equivalent of 2 g/L of glucose (colorimetric assay) in 60 minutes was determined.

EXAMPLE 1

Comparison of Stored *Trichoderma reesei* Mash

Example 1 presents the change in the activity of the enzymatic cocktail of a medium containing both said enzymatic cocktail and the cellulolytic microorganism *T. reesei*, termed the mash, stored for 3 weeks and having undergone three different treatments. This example shows that the FPU activity is conserved in the mash which has been placed under an atmosphere of $CO_2$ or $N_2$, while it is substantially reduced in that conserved in air.

An enzymatic cocktail was produced in a fermenter using *Trichoderma reesei* CL847 and by means of a conventional protocol described, for example, in patent application EP 1 690 944. The concentration of enzymatic cocktail obtained was 39.9 g/L and the activity was 32 FPU/mL.

The mash was divided into different pre-sterilized flasks, without separation of the cellulolytic microorganism and the supernatant containing the enzymatic cocktail.

In flask A, a gaseous stream comprising more than 99 molar % of $CO_2$ and containing less than 0.5 molar % of $O_2$ was bubbled through until the gas overhead contained less than 0.5 molar % $CO_2$. Said gaseous stream had been obtained by harvesting the degassing product from an alcoholic fermentation carried out elsewhere.

In flask B, a gaseous stream comprising more than 99 molar % of $N_2$ and containing less than 0.5 molar % of $O_2$ was bubbled through until the gas overhead contained less than 0.5 molar % $O_2$.

In flask C, the mash was stored in air in a sterile flask with a 0.2 μm filter.

The % $O_2$ was measured by gas phase chromatography (GPC) using a sample taken from the gas overhead.

The flasks were then stored at 33° C. for 3 weeks.

The activities obtained after three weeks are shown in Table 1. More than 90% of the activity was maintained in a $CO_2$ atmosphere or nitrogen atmosphere, while 50% of the activity was lost when the fungus was in the presence of air. The cellulolytic microorganism is thus indeed deactivated in the absence of air.

TABLE 1

Change in enzymatic activity

|  | Initial activity FPU/mL | Activity after 3 weeks FPU/mL |
|---|---|---|
| Flask A | 32.00 | 29.08 |
| Flask B |  | 30.44 |
| Flask C |  | 15.15 |

EXAMPLE 2

Comparison of Two SSFs

Example 2 compares two SSFs carried out at 33° C. using a mash containing both the cellulolytic microorganism and the enzymatic cocktail with or without the addition of $CO_2$ to the gas overhead.

Two SSFs were carried out using the enzyme production mash directly (enzymatic cocktail+cellulolytic microorganism) in the hydrolysis and fermentation reactor with a 30 mg dose of enzyme per gram of dry matter (DM). The percentage by weight of dry matter is the ratio of the weight of the sample obtained after drying at 105° C. for 24 hours over the initial weight of the sample. The weight of dry matter is the product of the percentage by weight of dry matter and the weight of the sample.

The experiment was carried out at 18% DM (wheat straw steam exploded under acid conditions, washed and dried) in a 2 L reactor. The temperature was adjusted to 33° C. and the pH was adjusted to 5 using 5 N sodium hydroxide (NaOH). The yeast was added 1 hour after starting hydrolysis, at a concentration of 0.5 g of yeast per kg of fermentation medium. The first SSF (SSF1) was carried out with a slight bubbling through of a gaseous stream comprising 99.8 molar % of $CO_2$ and 0.2 molar % of $O_2$. The second SSF (SSF2) was carried out without bubbling $CO_2$ through.

SSF1 finished with a final ethanol concentration of 40.2 g/L, while SSF2 finished with a final concentration of only 34.1 g/L. The SSF1 yield was greater than that of SSF2 by 17.9%. In the case of SSF2, the cellulolytic microorganism had consumed a portion of the sugar liberated by hydrolysis of the cellulose, causing the final yield for ethanol production to be reduced.

The invention claimed is:

1. A process for the production of an enzymatic cocktail and for the biochemical conversion of lignocellulosic materials with the enzymatic cocktail, said process comprising:
    producing the enzymatic cocktail with a cellulolytic microorganism to obtain a medium comprising the enzymatic cocktail and the cellulolytic microorganism;
    deactivating the cellulolytic microorganism in the medium by bringing a gaseous stream into contact with the medium obtained from producing the enzymatic cocktail which contains said microorganism, wherein the gaseous stream originates from a simultaneous saccharification and fermentation (SSF) step and wherein said gaseous stream comprises more than 25% by weight of $CO_2$ and comprising less than 0.5 molar % of $O_2$, and whereby the gaseous stream deactivates the cellulolytic microorganism in the medium; and
    without separating the cellulolytic microorganism from the enzymatic cocktail in the medium, contacting the medium with lignocellulosic materials to effect biochemical conversion of the lignocellulosic materials.

2. The process according to claim 1, wherein the gaseous stream has undergone a treatment for reducing its ethanol and volatile organic compounds content by at least 25% before the contact step.

3. The process according to claim 2, wherein the treatment is washing said gaseous stream with water.

4. The process according to claim 1, wherein the cellulolytic microorganism is selected from strains of fungi belonging to the genera *Trichoderma*, *Aspergillus*, *Penicillium* or *Schizophyllum*.

5. The process according to claim 4, wherein the cellulolytic microorganism belongs to the species *Trichoderma reesei*.

6. The process according to claim 1, wherein the gaseous stream comprises less than 0.25 molar % of $O_2$.

7. The process according to claim 1, wherein the contacting of the medium with lignocellulosic materials for biochemically converting the lignocellulosic materials is an SSF step comprising saccharification and fermentation of the lignocellulosic materials.

8. The process according to claim 7, wherein the SSF comprises saccharification of the lignocellulosic materials to products comprising glucose and fermentation of the glucose to ethanol.

9. The process according to claim 1, wherein the step of bringing the gaseous stream into contact with the medium is carried out during the step for producing the enzymatic cocktail.

10. The process according to claim 1, wherein the step of bringing the gaseous stream into contact with the medium is carried out during the step for biochemical conversion of the lignocellulosic materials.

11. The process according to claim 1, wherein the step of bringing the gaseous stream into contact with the medium is carried out between the step for producing the enzymatic cocktail and the step for biochemical conversion of the lignocellulosic materials.

12. The process according to claim 7, wherein the step of bringing the gaseous stream into contact with the medium is carried out in the SSF step for biochemical conversion of the lignocellulosic materials.

* * * * *